United States Patent [19]

McMahon et al.

[11] 4,420,567

[45] Dec. 13, 1983

[54] HYDRIDE GAS DETECTING TAPE

[75] Inventors: Roberta McMahon, Chicago; Franco F. Fiorese, Elmhurst, both of Ill.

[73] Assignee: MDA Scientific, Inc., Glenview, Ill.

[21] Appl. No.: 313,651

[22] Filed: Oct. 22, 1981

[51] Int. Cl.³ ............................................. G01N 31/08
[52] U.S. Cl. ...................................... 436/169; 436/73; 436/103; 436/106; 436/109; 436/167; 422/56
[58] Field of Search ................ 436/73, 103, 106, 109, 436/167, 169; 422/56

[56] References Cited

U.S. PATENT DOCUMENTS 4,211,532  7/1980  Tobari et al. ..................... 422/56 X

OTHER PUBLICATIONS

Nelson and Milum, "Rapid Determination of Phosphine in Air", *Anal. Chem.*, 29, 1665 (1957).
Patty, Industrial Hygiene and Toxicology, 2nd Ed., 944–998 Interscience Publishers, New York (1962).
Hughes and Jones, "The Estimation of Phosphine in Air," *American Industrial Hygiene Assn. Journal*, 24, 164 (1963).
DuBois and Monkman, "Determination of Arsenic in Air and Biological Materials, *American Industrial Hygiene Assn. Journal*, 292 (1961).
Jacobs, "Analytical Chemistry of Industrial Poisons, Hazards and Solvents", 2nd Ed., 246, Interscience Publishers, New York, (1949).
Muthu et al., "Detector for Phosphine at Permissible Levels in Air", *J. Agr. Food Chem.*, 21, 184 (1973).

*Primary Examiner*—Ferris H. Lander
*Attorney, Agent, or Firm*—McDougall, Hersh & Scott

[57] ABSTRACT

A tape coated with an adsorbent and impregnated with a processing solution which includes silver nitrate, an acid, an alcohol and a glycol is a sensitive detecting means for hydride gases and is stable upon exposure to light.

11 Claims, 3 Drawing Figures

HYDRIDE GAS DETECTING TAPE

BACKGROUND OF THE INVENTION

The present invention relates in general to the detection and monitoring of toxic vapors and gases, and in particular, to the detection and monitoring of hydride gases in industrial environments. A variety of toxic gaseous hydrides are used or formed in industrial processing and manufacturing.

Metallic hydrides, such as arsine ($AsH_3$), and phosphine ($PH_3$), are highly poisonous, colorless, non-irritating gases often having a mild garlic odor. These gases can be formed in aqueous solution, and are slightly soluble in alcohol and alkaline solutions. For example, when nascent (freshly formed) hydrogen is generated in the presence of arsenic or when water reacts with a metallic arsenide, arsine evolves. Most cases of arsine and phosphine poisoning have been associated with the use of acids and crude metals, one or both of which contained arsenic or phosphorous as an impurity.

In an industrial setting, hydride gas poisoning can also result from the accidental formation of the gas. As an example, most reported cases of exposure to arsine have occurred during the smelting and refining of metals since ores contaminated with arsenic can liberate arsine when treated with acid. There are many other situations, however, where exposures to lethal concentrations of hydride gases have been reported including galvanizing, soldering, etching and lead plating operations. Arsine can also be produced by fungi, particularly in sewage, in the presence of arsenic. Moreover, the renewed interest in coal as an energy source may increase the number of exposures to arsine, because coal contains considerable quantities of arsenic.

Like arsine, phosphine is a colorless, poisonous gas that is soluble in water, alcohol and alkaline solutions. Phosphine is also soluble in ether. Similar to arsine, phosphine can be formed by the generation of nascent hydrogen in the presence of phosphorous, or by the action of acids or water on metallic phosphides. Arsine and phosphine are produced commercially for use as reagents in organic synthesis, and as "dopants" or impregnants in the processing of solid state electronic components.

In addition to arsine and phosphine, other hydride gases including stibine ($SbH_3$), diborane ($B_2H_6$) and germane ($GeH_4$) are often used as dopant gases in the manufacture of semiconductors. Semiconductors comprise silicon wafers which are doped or impregnated with high concentrations of gases that serve as impurities to form controlled current bands for the flow of electrons. Ideally, the gases are applied as dopants in an enclosed system such as a high temperature diffusion furnace or an ion implantation assembly; but despite safety precautions, the potential still exists for gas leakage or a cylinder explosion. Such an accident poses a serious health threat.

The need exists, therefore, for a method to detect and monitor hydride gas concentrations in industrial environments. In the past, a semi-quantitative method using paper tapes which have been impregnated with mercuric bromide ($HgBr_2$) or mercuric chloride ($HgCl_2$) has been used in the detection of hydride gases such as arsine and phosphine. A yellow stain is produced on the tape upon exposure to the gas according to the following reaction:

$$M_xH_n + nHgCl_2 \rightarrow M_x(HgCl)_n + nHCl$$

wherein M represents a metal, x is the integer 1 or 2 and n is an integer from 3 to 6.

The optical properties of this stain, however, do not permit the detection of low concentrations of hydride gases. In fact, only concentrations in excess of ten times the threshold limit value (TLV) can be detected in the preferred sampling time of five minutes. As used herein, the "threshold limit value" means the maximum allowable concentration for prolonged human exposure to the gas as determined by the American Congress of Government Industrial Hygienists.

Devices directed to this need for industrial safety are the subject of U.S. Pat. No. 4,073,621 to Bull et al. and application Ser. No. 567,379 filed Apr. 11, 1975, now abandoned. Both references are assigned to the present assignee and are hereby incorporated by reference.

Specifically, the patent to Bull et al. describes a reader recorder for toxic gas concentration tapes that produces a chart record of gas concentration versus time and the total eight hour dose of the gas as determined from the tape exposed in a gas monitor. The exposed tape is passed through an optical reader portion of the device and the measured stain intensity is recorded versus time to immediately provide an easily read, permanent record of gas concentration as a function of time. While the concentration versus time function is being produced, the device also integrates the concentration as a function of time to determine the total dose for a given period; e.g., an eight hour work shift. This total dose is recorded on the chart in bar graph format at the end of the concentration versus time plot.

Application Ser. No. 567,379, on the other hand, discloses a portable miniaturized monitor that exposes a roll of gas sensitive chemically treated tape in the breathing zone of a worker. Upon exposure to the gas, a stain developes on a portion of the tape which is later read on a readout device such as that described by Bull et al. Since reading of the tape occurs after exposure, the monitor includes means to prevent contamination of adjacent layers of tape. At the end of the work shift, the exposed tape is removed from the monitor and placed into the reader recorder to produce a permanent graphic display of concentration versus time in total dose values. From this information a time-weighted average exposure level as well as excursions above a predetermined maximum ceiling can be determined.

A number of direct methods have also been developed to determine phosphine concentration using the ability of phosphine to reduce silver salts to metallic silver compounds. The resulting color change can be measured on silica gel (Nelson, J. P. and Milum, A. J., "Rapid Determination of Phosphine in Air", *Analytical Chemistry*, 29, 1665 (1957)) or on paper. In addition, the reduced silver can be measured chemically. (Jones, A. T. et al., "Environmental and Clinical Aspects of Fumigation of Bulk Wheat with Aluminum Phosphide Containing Tablets", New South Wales Division of Occupational Health, Australia (1962). Arsine concentrations can be determined in a similar manner.

Another hydride gas, stibine is used only to a minor extent in the chemical industry, in metal polishing and decoration, and in the pharmaceutical industry. Serious hygienic problems have not been reported regarding the use of stibine. However, liberation of stibine vapors can occur during the charging of storage batteries, resulting from the action of nascent hydrogen on the antimony present in the battery plates. Stibine can also be generated from antimony-containing alloys that have been treated with a reducing acid. No direct reading instrument is currently available for the quantitative determination of stibine concentrations; but a rapid semi-quantitative evaluation can be performed by means of silver nitrate test papers. (Patty, R. A., Industrial Hygiene and Toxicology, 2nd Ed., Interscience Publishers, New York (1963).) A more precise method involves absorption of the gas in mercuric chloride solution, followed by colorimetric determination with rhodamine B. (Id.)

Therefore, it is known that silver nitrate ($AgNO_3$) will react with certain metal hydrides whereby silver nitrate is reduced and silver compounds are precipitated forming a characteristic black or dark brown color. Whereas this method of detecting concentrations of hydride gases has been proposed, silver nitrate is extremely light sensitive and unstable. A detecting tape coated with silver nitrate turns brown within a 24 hour period, even when sealed in a black, lightproof container. The tape, therefore, must be stable to light to be processed and analyzed. Indeed, a commercially useful hydride gas detecting tape should be stable for at least three to six months when stored at room temperature and protected from exposure to light and air. The tape should also be stable for at least several days upon exposure to light. The present invention is directed to these problems.

SUMMARY OF THE INVENTION

The present invention relates to a tape coated with an adsorbent and impregnated with a processing solution which includes silver nitrate, an acid, an alcohol and a glycol that is stable to light for detecting and monitoring concentrations of hydride gases. A chart record of gas concentration versus time and total 8 hour dose as determined from the exposed tape can be immediately prepared. The intensity of the stain on the tape is directly related to the concentration of gas.

The exposed tape of the invention is passed through the optical reader portion of a reader recorder and the measured stain intensity is recorded with time to provide an easily read, permanent record of gas concentration versus time. While the concentration versus time function is being produced, the concentration as a function of time is integrated to determine the total dose for the given period, i.e., 8 hours. This total dose is recorded on the chart in bar graph format at the end of the concentration versus time plot.

DETAILED DESCRIPTION OF THE INVENTION

Figure 1:
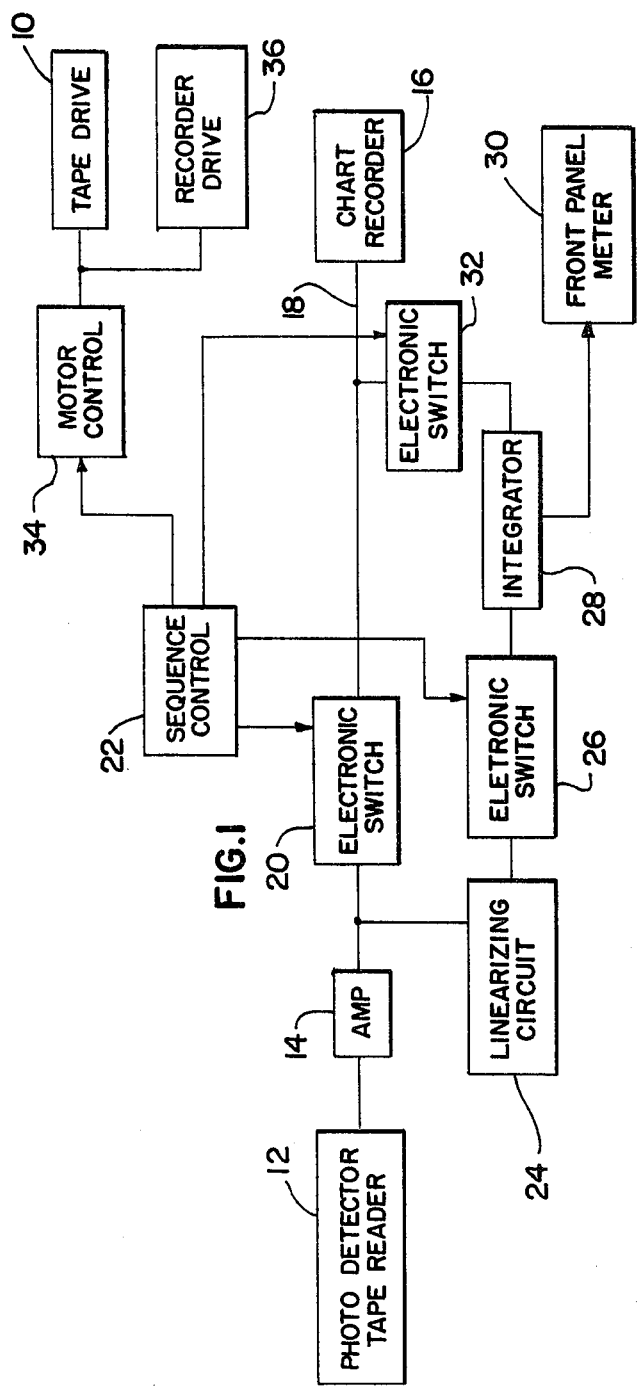
FIG. 1 is a block diagram of a reader recorder for use in the present invention.

The present invention relates to a detecting tape for monitoring the presence of hydride gases in the environment. A porous tape is coated with an adsorbent material and is impregnated with a tape processing solution comprising silver nitrate, an organic or inorganic acid, an alcohol and a glycol.

An adsorbent is a solid surface comprising particles upon which gases, liquid or dissolved substances can condense. Adsorbents suitable for use in the present invention include silicic acid ($H_2SiO_3$), FLORISIL (an activated magnesium silicate described in U.S. Pat. No. 2,393,625), magnesium oxide (MgO) and aluminum oxide ($Al_2O_3$). A porous tape made of cellulose or the like is coated with the adsorbent. In this manner, the tape includes solid particles upon which surface adsorption of the hydride gas can occur. As will be described, the hydride gas is adsorbed on the surface of the tape and reacts with the silver nitrate to form a stain the intensity of which can be measured quantitatively by an optics system to determine the concentration of the gas.

The adsorbent coated tape is then treated with the processing solution which contains the organic or inorganic acid. The resulting tape is more stable upon exposure to light and retains a white background for a longer period of time than if no acid were present in the solution. This increased stability is due to the acid induced deactivation of alcoholic groups present in the cellulose of the tape. Nitric acid, for instance, either oxidizes or combines with these alcoholic groups, rendering them unavailable for subsequent reaction with silver nitrate. Without acid treatment, the active alcoholic sites could potentially reduce silver nitrate, yielding a brown tape background.

The processing solution has a silver nitrate concentration between 0.5 and 2.0% by weight. It has been determined that a tape treated with a 0.5% silver nitrate solution is saturated and completely reacts with the hydride gas in a short period of time, even at relatively low gas concentrations. Moreover, depending on the concentration of hydride present, a tape prepared with a 2.0% silver nitrate solution can yield a stain that is too intense to be precisely measured by the equipment described herein. In the preferred embodiment, a tape processed with a 1.0% by weight silver nitrate solution is used.

Inorganic acids including hydrochloric, sulfuric and phosphoric were used in the preparation of tape processing solutions. An organic acid such as glacial acetic or trichloroacetic is also suitable. The addition of hydrochloric acid to the tape solution causes the formation and precipitation of silver chloride which is unreactive with hydride gases. Sulfuric acid in combination with the tape processing solution causes the precipitation of silver sulfate, although some silver nitrate remains in solution. A tape treated with the sulfuric acid remains white when protected from light, but is only 30% as reactive to arsine and phosphine as a nitric acid containing tape. A trichloroacetic acid tape, on the other hand, is 50% as reactive to hydride gases as a nitric acid tape, but turns purple after only one day of exposure to air and light. Thus, nitric acid is the preferred inorganic acid for tape stabilization.

Based on these observations, a series of tapes were prepared with nitric acid so that each tape was treated with a processing solution having a different concentration of the acid. The acid content of the processing solutions ranged from 0.13 to 2.7% by volume nitric acid. After storage in black bags for over six months, all of the tapes retained their original white background.

While the addition of acid concentrations as low as 0.13% by volume will stabilize the tape, higher acid concentrations preserve the tape for longer periods of time upon exposure of the tape to light or air. When stored under protected conditions out of contact with light and air, tapes prepared with a low acid content are as stable as those prepared with a high acid content. Since extreme amounts of acid eventually degrade the paper tape, it was determined that a 0.1–0.5% nitric acid concentration was preferred for tape processing.

The processing solution of the present invention comprises silver nitrate, the organic or inorganic acid as previously described, an alcohol and a glycol. The alcohol was selected as the solvent because it allows the tape to dry readily when processed relative to a water-based solution. If the tape is not adequately dried, its tensile strength is poor. The glycol increases the adsorbent ability of the tape by keeping the tape moist enough to allow the intended reaction between incoming hydride gas and the tape reagents to occur. While the solution could include any alcohol and glycol, for purposes of illustration, the use of methanol and glycerol is described. Specifically, the tape processing solution of this example included the following:

1.5 ml. Conc. Nitric Acid;
25 ml. Glycerol; and
224 ml. Methanol.

2.5 grams silver nitrate was added to the solution and a paper tape coated with silicic acid (or silica gel) was immersed into the processing solution.

A tape prepared in this manner maintains a white background for at least six months under normal storage conditions at room temperature with protection from light. In addition, after six months the tape still displays its original sensitivity ($\pm 10\%$) to hydride gases.

It will be understood that other alcohols including ethyl alcohol, isopropyl alcohol and the like can be used in the formulation of the present invention. Likewise, glycols such as ethylene glycol, propylene glycol and trimethylene glycol are suitable. The use of methanol and glycerol, however, is preferred for economic reasons. Moreover, the processing solution can include from 5 to 20% glycol by weight whereby the composition range by weight of the processing solution is:

0.1–5% acid;
5–20% glycol; and
94.9–75% alcohol.

For example, when nitric acid, glycerol and methanol are used, the preferred mixture by volume is 1% nitric acid, 10% glycerol and 89% methanol.

Hydride gas detecting tapes prepared by this procedure when used in an apparatus as described by Bull et al. in U.S. Pat. No. 4,073,621 can detect gas concentrations as low as 0.02 ppm arsine or 0.05 ppm phosphine in a sampling time of three minutes. The threshold limit values for arsine and phosphine are 0.05 ppm and 0.30 ppm, respectively.

Referring now to FIG. 1, a block diagram of a device for use in reading and recording the tape of the present invention is illustrated. An exposed tape, sensitive to a hydride gas, is produced as previously described and is placed in a tape reader section which includes a tape drive 10 for moving the tape past a photocell optical section 12. The photocell optical reader 12 utilizes the technique of applying a source of light of known intensity to the tape and measuring the light reflected from the tape as an indication of stain intensity. In order to maintain the light at the proper intensity, a reference photocell is employed for measuring the reflected light from an unstained portion of the tape.

The output from the photocell optical reader 12 is provided to an amplifier 14 to increase the signal level for use throughout the balance of the circuit. From amplifier 14 the photocell signal which is a direct function of the stain intensity of the tape is provided to a chart recorder 16 via line 18 whenever an electronic switch 20 is operated by a sequence control circuit 22.

The output of the amplifier 14 is also provided to a linearizing circuit 24. The linearizing circuit is described in greater detail in the Bull reference. Briefly, however, its purpose is to produce a linear relationship between stain intensity and the output voltage from amplifier 14 so that a straight-forward integration of the area under a stain intensity versus time curve may be performed. The output of the linearizing circuit 24 is connected via an electronic switch 26 to an integrator 28. The output of the integrator is provided to a front panel meter 30 so that the value may be continuously monitored during the operation of the invention. By means of an electronic switch 32 the output of the integrator is also provided to the chart recorder 16 so that at the end of a tape segment the total dosage may be printed out directly by the chart recorder. When switch 32 is utilized to connect the integrator 28 to the chart recorder, switch 20 is opened to disconnect the direct signal.

The sequence control 22 in addition to correctly operating the electronic switches 20, 26 and 32 also includes necessary timing logic for operating the mechanical sections of the invention. Specifically, timing logic is provided for turning the drive motor on and off via motor control 34. A primary advantage of this device is a directly proportional relationship between distance on the tape being read and distance on the chart or graph being produced by the chart recorder. This is preferably achieved by providing a single motor to drive both the tape and the chart. Thus, there is a known relationship between the tape drive and the chart recorder drive 36. Desirably, this relationship may be some whole integer ratio, such as one to one or two to one so that a given segment of tape which, for example, may represent an eight hour shift, will repeatedly produce a given length of output from the chart recorder. That output may then be characterized as the graph of an 8 hour shift of exposure to a hydride gas. Similarly, under these circumstances, the integral of the area under such a curve is representative of the total dosage over that period of time. From such information the time weighted average can be rapidly calculated by dividing the total dose for the given period by the number of hours in the period.

Figure 2:
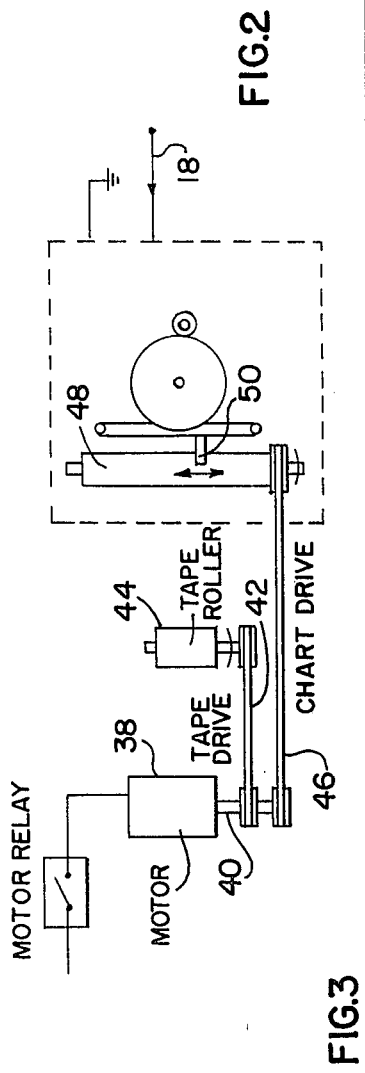
FIG. 2 is a simplified drawing of the mechanical linkage between the drive motor, the tape drive and the recorder chart drive.

Turning now to FIG. 2, a schematic of the mechanical chart drive according to the present invention is illustrated. The tape and chart paper recorder are both driven from the motor 38 which has an output shaft 40. From the output shaft the tape drive employs a nonslip belt 42 for driving a roller 44 which feeds the tape past the optics portion of the device. Also deriving its power from the shaft 40 is a nonslip belt 46 which is utilized for driving a roll 48 which controls the passage of chart paper past a recording pen 50. The recording pen 50 is driven in the direction indicated by the arrows by the signal applied to the chart paper on the line 18. This represents the Y coordinate on the graph of FIG. 3. Due to the fact that the tape drive and the recorder drive are connected to the same output shaft 40 there is a definite fixed relationship between movement of the tape and movement of the chart paper. This is highly desirable for the following reasons. When the recorder and tape are driven in a fixed relationship as, for example, a one to one relationship by a synchronous motor, distance along the tape and thus along the chart record corresponds to time of exposure. Events of interest can be related to time of occurrence, an important advantage over prior systems. This also permits the sequencing of the invention by internal timing components.

If the tape during exposure travels at two centimeters per hour, then 16 centimeters of tape will be exposed during a normal eight hour work shift. When read, the tape and chart can travel at, for example, one centimeter per second. Therefore, it will take 16 seconds to read an eight hour tape.

Figure 3:
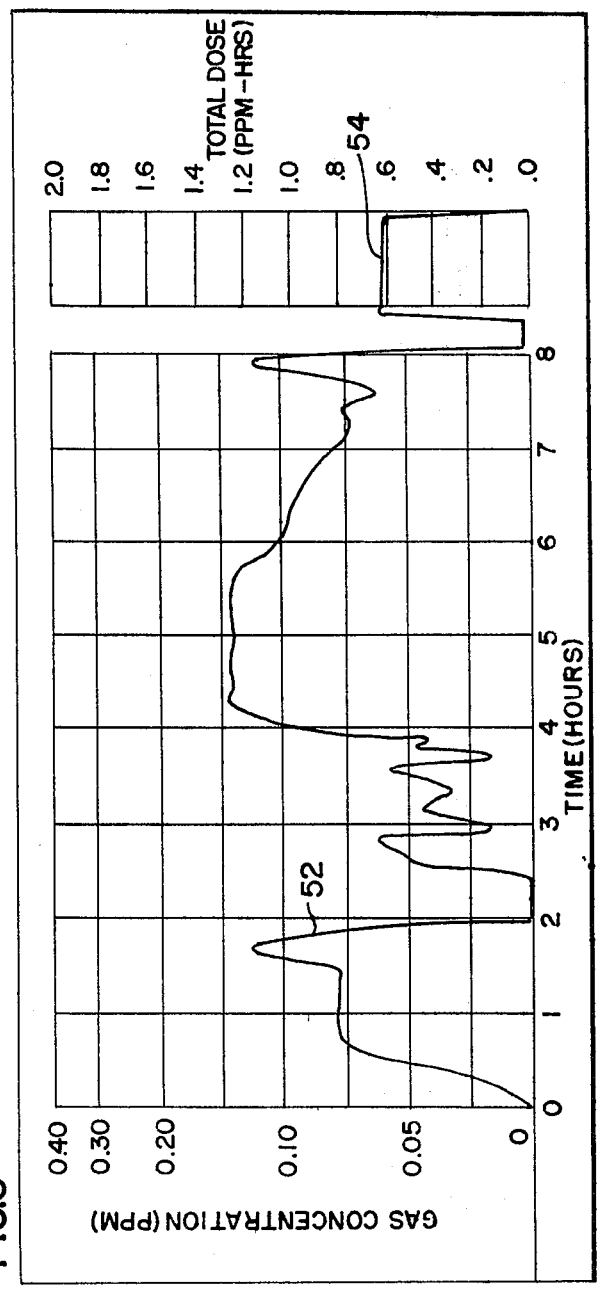
FIG. 3 is an illustration of a typical time versus concentration graph and of a bar chart printout of total hydride gas concentration.

In FIG. 3, the output from the chart recorder 16 is illustrated. By coupling the chart recorder with the tape drive, the output from the chart recorder can be calibrated in eight hour segments to represent a worker's shift. FIG. 3 shows a typical wave form of exposure for a worker over an eight hour period. The wave form 52 shows a variety of concentration values during the eight hour shift with three excursions above the 0.10 parts per million concentration level. At the end of the eight hour shift the recorder pen returns to zero when disconnected from the amplifier 14. Subsequently, when the integrator is connected to the recorder it prints out when the integrator is connected to the recorder it prints out a bar chart wave form 54 indicative of the integral of the area under the curve 52. This value is the total dose for eight hours. To obtain the time weighted average exposure it is only necessary to divide the bar chart by the number of hours or exposure.

The tape of this invention can be used to measure hydride gas concentrations in most environments. But since strong reducing agents including hydrogen sulfide ($H_2S$) and hydrazine ($N_2H_4$) can react with silver nitrate to produce a characteristic brown stain, the tape must be protected from exposure to these reagents. Interference from hydrogen sulfide can be eliminated by inserting a lead acetate prefilter in the sampling line of the device. The presence of hydrazine, however, does not present a practical problem since hydrazine is not often used on an industrial scale and is not a by-product of most manufacturing processes.

An additional problem of negative interference or stain bleaching, however, can occur if high concentrations of acids are present in the sampled air; but the acid concentrations required to produce stain bleaching are so high that such a condition would of itself pose a serious health hazard to anyone breathing the atmosphere. Therefore, elevated atmospheric acid concentrations do not constitute a significant source of interference.

It will be understood that various changes and modifications can be made in the details of the above procedure, formulation and use, without departing from the spirit of the invention, particularly as defined in the following claims.

We claim:

1. A substrate for detecting hydride gases comprising a solid absorbent material and a detector composition impregnating the absorbent material, said detector composition consisting essentially of silver nitrate, an organic or inorganic acid to stabilize the silver nitrate and a glycol to maintain the substrate in a moist condition whereby the substrate is capable of reaction with a hydride gas for the development of color as a measure of the hydride concentration.

2. A substrate according to claim 1 wherein said adsorbent material is selected from the group consisting of silicic acid, magnesium silicate, magnesium oxide and aluminum oxide.

3. A substrate according to claim 1 wherein said absorbent material is impregnated with silver nitrate in an amount within the range of 0.5–2.0% by weight of silver nitrate in the solution.

4. A substrate according to claim 1 wherein said acid is selected from the group consisting of nitric acid, sulfuric acid, phosphoric acid, glacial acetic acid and trichloroacetic acid.

5. A substrate according to claim 1 wherein said acid is present in an amount within the range of 0.1–5.0% by volume of the solution.

6. A substrate according to claim 1 wherein said glycol is selected from the group consisting of ethylene glycol, propylene glycol, trimethylene glycol and glycerol.

7. A substrate according to claim 1 wherein said glycol is present in an amount within the range of 5–20% by volume of the solution.

8. A method for detecting hydride gases comprising:
(a) contacting a hydride-containing gas with a substrate for detecting hydride gases comprising a solid absorbent material impregnated with a detector composition, said detector composition consisting essentially of silver nitrate, an organic or inorganic acid to stabilize the silver nitrate and a glycol to maintain the substrate in a moist condition whereby the substrate is capable of reaction with a hydride-containing gas for the development of color;
(b) sampling said hydride-containing gas over a given period of time by allowing diffusion of said gas onto the porous member to produce the detectable color; and
(c) determining the intensity of the color as a measure of the concentration of hydride gases in the atmosphere.

9. A method in accordance with claim 8 wherein the contacting, sampling and measuring is performed continuously.

10. A method in accordance with claim 8 wherein the intensity of the color is determined electronically to produce a graph of gas concentration versus time over a known time period.

11. A method for detecting and measuring hydride gases comprising the steps of contacting a hydride-containing gas with a solid absorbent material impregnated with a protector composition, said detector composition consisting essentially of silver nitrate, an organic or inorganic acid to stabilize the silver nitrate and a glycol to maintain the substrate in a moist condition or reaction with a hydride gas whereby the substrate develops color in response to a reaction with hydride gas, and determining the intensity of the color developed as a measure of the concentration of the hydride gas.

* * * * *

UNITED STATES PATENT OFFICE
CERTIFICATE OF CORRECTION

Patent No. 4,420,567　　　　　　　　Dated December 13, 1983

Inventor(s) Roberta McMahon & Franco F. Fiorese

It is certified that error appears in the above-identified patent and that said Letters Patent are hereby corrected as shown below:

Claim 1, line 3, "absorbent" should read --adsorbent--.

Claim 3, lines 1 and 2, "absorbent" should read --adsorbent--.

Claim 8, line 4, "absorbent" should read --adsorbent--.

Claim 11, line 3, "absorbent" should read --adsorbent--.

Claim 11, line 4, "protector" should read --detector--.

Claim 11, line 7, "or" should read --for--.

Signed and Sealed this

Seventh Day of May 1985

[SEAL]

Attest:

DONALD J. QUIGG

Attesting Officer　　Acting Commissioner of Patents and Trademarks